US009044527B2

(12) United States Patent
Neas et al.

(10) Patent No.: US 9,044,527 B2
(45) Date of Patent: Jun. 2, 2015

(54) WOUND CARE PRODUCTS WITH PERACID COMPOSITIONS

(71) Applicant: CHD Bioscience, Inc., Fort Collins, CO (US)

(72) Inventors: Edwin D. Neas, Nunn, CO (US); Michael K. Handley, Windsor, CO (US); Kevin S. Marchitto, Golden, CO (US); Stephen T. Flock, Arvada, CO (US)

(73) Assignee: CHD Bioscience, Inc., Fort Collins, CO (US)

(*) Notice: Subject to any disclaimer, the term of this patent is extended or adjusted under 35 U.S.C. 154(b) by 38 days.

(21) Appl. No.: 13/967,080

(22) Filed: Aug. 14, 2013

(65) Prior Publication Data
US 2013/0330397 A1 Dec. 12, 2013

Related U.S. Application Data

(63) Continuation-in-part of application No. 13/400,013, filed on Feb. 17, 2012.

(60) Provisional application No. 61/444,111, filed on Feb. 17, 2011, provisional application No. 61/565,986, filed on Dec. 2, 2011, provisional application No. 61/683,054, filed on Aug. 14, 2012, provisional application No. 61/693,009, filed on Aug. 24, 2012, provisional application No. 61/715,725, filed on Oct. 18, 2012.

(51) Int. Cl.
| *A61K 31/327* | (2006.01) |
| *A61K 9/70* | (2006.01) |
| *A01N 37/42* | (2006.01) |
| *A61L 26/00* | (2006.01) |
| *A61K 33/40* | (2006.01) |
| *A61K 31/19* | (2006.01) |
| *A61K 31/22* | (2006.01) |
| *A61K 45/06* | (2006.01) |
| *A01N 59/00* | (2006.01) |
| *A61K 47/32* | (2006.01) |
| *A61K 47/36* | (2006.01) |

(52) U.S. Cl.
CPC .......... *A61L 26/0066* (2013.01); *A61K 33/40* (2013.01); *A61K 31/327* (2013.01); *A61K 31/19* (2013.01); *A61K 31/22* (2013.01); *A61K 45/06* (2013.01); *A01N 37/42* (2013.01); *A01N 59/00* (2013.01); *A61K 47/32* (2013.01); *A61K 47/36* (2013.01); *A61K 9/7007* (2013.01)

(58) Field of Classification Search
CPC ... A61K 31/327; A61K 9/7007; A01N 37/42; A61L 26/0066
See application file for complete search history.

(56) References Cited

U.S. PATENT DOCUMENTS

| 2,806,045 | A | 9/1957 | Gross |
| 3,169,986 | A | 2/1965 | Reginald et al. |
| 3,829,468 | A | 8/1974 | Serad et al. |
| 3,978,032 | A | 8/1976 | Manner |
| 4,004,977 | A | 1/1977 | Kato et al. |
| 4,008,175 | A | 2/1977 | Barter |
| 5,597,791 | A | 1/1997 | Richards et al. |
| 5,718,910 | A | 2/1998 | Oakes et al. |
| 6,325,968 | B1 | 12/2001 | Fricker et al. |
| 6,627,657 | B1 * | 9/2003 | Hilgren et al. ............. 514/553 |
| 6,943,190 | B2 | 9/2005 | Fink et al. |
| 6,991,685 | B2 | 1/2006 | Kravitz et al. |
| 8,349,449 | B2 * | 1/2013 | Privitera et al. ............. 428/364 |
| 8,426,634 | B2 | 4/2013 | Neas et al. |
| 8,445,717 | B2 | 5/2013 | Neas et al. |
| 2001/0016604 | A1 | 8/2001 | Yu et al. |
| 2004/0176267 | A1 | 9/2004 | Hobson et al. |
| 2005/0197397 | A1 | 9/2005 | Martin |
| 2007/0048345 | A1 | 3/2007 | Huang et al. |
| 2007/0056904 | A1 | 3/2007 | Hogt et al. |
| 2007/0082832 | A1 | 4/2007 | DiCosimo et al. |
| 2007/0148214 | A1 | 6/2007 | Cullen et al. |

(Continued)

FOREIGN PATENT DOCUMENTS

| EP | 0320219 | 6/1989 |
| WO | WO 91/13058 | 9/1991 |

(Continued)

OTHER PUBLICATIONS

International Search Report prepared by the U.S. Patent Office as International Searching Authority for PCT International Patent Application No. PCT/US2013/54968, mailed Jan. 14, 2014, 20 pages.
International Search Report for PCT/US13/65769 dated Apr. 17, 2014, 46 pages.
Bunton (1949) Nature 163:444 "Oxidation of α-Diketones and α-Keto-Acids by Hydrogen Peroxide".
Cooper, et al. (1983) Chem. Rev. 83:321-358 "Synthesis and Properties of the α-Keto Acids".

(Continued)

Primary Examiner — Sean Basquill
Assistant Examiner — Andrew S Rosenthal
(74) Attorney, Agent, or Firm — Volpe and Koenig, P.C.

(57) ABSTRACT

Methods have been developed for incorporation of a peracid compound into or on wound application matrices, such as bandages or dressings, and other matrices which will favorably impact wound healing and help eliminate microbial infection. The peracid compound comprises a base compound that is metabolically pertinent to wound healing, the oxidized form of the base compound (a peracid), and an appropriate oxidizer, such as hydrogen peroxide. In addition, other excipients with wound healing potential, such as esters of the base compound, may be added to the peracid compound. The combination peracid-wound application matrices can be used to disinfect and heal various wound types with designed time release of the peracid compound.

27 Claims, 8 Drawing Sheets

(56) References Cited

U.S. PATENT DOCUMENTS

| | | | |
|---|---|---|---|
| 2007/0202069 | A1 | 8/2007 | Tamareselvy et al. |
| 2008/0233069 | A1 | 9/2008 | Tamareselvy et al. |
| 2009/0145859 | A1 | 6/2009 | Man et al. |
| 2009/0239947 | A1 | 9/2009 | Dai et al. |
| 2010/0040608 | A1 | 2/2010 | Wahren-Herlenius et al. |
| 2010/0108942 | A1* | 5/2010 | Man et al. ............. 252/186.26 |
| 2010/0125104 | A1 | 5/2010 | Neas et al. |
| 2011/0117178 | A1 | 5/2011 | Junginger |
| 2011/0165261 | A1* | 7/2011 | Derby et al. ............. 424/616 |
| 2011/0301070 | A1 | 12/2011 | Ochomogo et al. |
| 2011/0305872 | A1 | 12/2011 | Li et al. |
| 2012/0021486 | A1 | 1/2012 | Dinu et al. |
| 2012/0213835 | A1 | 8/2012 | Neas et al. |
| 2013/0224307 | A1 | 8/2013 | Neas et al. |
| 2013/0251820 | A1 | 9/2013 | Neas et al. |
| 2013/0330397 | A1 | 12/2013 | Neas et al. |

FOREIGN PATENT DOCUMENTS

| | | |
|---|---|---|
| WO | WO 93/01716 | 2/1993 |
| WO | WO 2006/093792 | 9/2006 |
| WO | WO 2007/018923 | 2/2007 |
| WO | WO 2010/059531 | 5/2010 |
| WO | WO 2011/129829 | 10/2011 |
| WO | WO 2012/112951 | 8/2012 |

OTHER PUBLICATIONS

Desagher et al. (1997) The Journal of Neuroscience 17(23):9060-9067 "Pyruvate Protects Neurons against Hydrogen Peroxide-Induced Toxicity".

Estes et al. (2010) Expert Rev Anti Infect Ther 8(3):325-338 "Present and future therapeutic strategies for melioidosis and glanders" doi:10.1586/eri.10.4.

European Search Report for 09828061.3 mailed Sep. 24, 2012, 7 pages.

Fink (2007) Current Drug Targets 8:515-518 "Ethyl Pyruvate: A Novel Treatment for Sepsis".

Fink (2007) J Intern Med 261:349-362 "Ethyl pyruvate: a novel anti-inflammatory agent".

Greenspan (1947) Industrial and Engineering Chemistry 39:847-848 "Oxidation Reactions with Aliphatic Peracids" XP-002683108.

Hanson (1987) Department of Biological Sciences 64(7):591-595 "Decarboxylation of α-Keto Acids".

Holleman (1904) Recl. Trav. Chim. Pays-bas Belg. 23 (English Abstract).

International Search Report for PCT/US09/64450 dated May 31, 2010, 5 pages.

International Search Report for PCT/US10/31245 dated Jan. 21, 2011, 5 pages.

International Search Report for PCT/US12/25736 dated May 29, 2012, 1 page.

Lever and Mackenzie (2007) BMJ 335:879-883 "Sepsis: definition, epidemiology, and diagnosis".

Miyaji et al. (2003) Kidney International 64:1620-1631 "Ethyl pyruvate decreases sepsis-induced acute renal failure and multiple organ damage in aged mice".

Nath et al. (1995) The American Physiological Society C227-C236 "α-Ketoacids scavenge $H_2O_2$ in vitro and in vivo and reduce menadione-induced DNA injury and cytotoxicity".

Neas et al. (2013) Power Point Presentation presented on Jan. 3, 2013 for U.S. Appl. No. 12/618,605 "CHD Bioscience: Answers for infectious disease: CHD Meeting with USPTO" 31 slides.

Panda and Patnaik (2001) Bull. Korean Chem. Soc. 22(8):909-913 "Peroxy Acid Oxidations: A Kinetic and Mechanistic Study of Oxidative Decarboxylation of α-Keto Acids by Peroxomonophosphoric Acid".

Swern (1948) Eastern Regional Research Laboratory 1-68 "Organic Peracids".

Vlachou and Berth-Jones (2007) Journal of Dermatological Treatment 18:175-177 "Nail psoriasis improvement in a patient treated with fumaric acid esters".

Vlessis et al. (1990) Biochemical and Biophysical Research Communications 170(3):1281-1287 "Importance of Spontaneous α-Ketoacid Decarboxylation in Experiments Involving Peroxide".

Wang et al. (1999) Science 285:248-251 "HMG-1 as a Late Mediator of Endotoxin Lethality in Mice".

International Search Report for PCT/US13/65782 dated Feb. 19, 2014, 32 pages.

North Cell Pharm pamphlet "Effect of Alpha Keto Acids Including Sodium Pyruvate on Reducing and Regulating the Inflammatory Agents Needed in the Healing of Infected and Non-Infected Wounds" [retrieved on Mar. 17, 2014 from http://www.northcellpharma.com/NCP_Research_Devel_Data.pdf].

Chen et al., "Extracellular HMGB1 as a Proinflammatory Cytokine," Journal of Interferon & Cytokine Research 24:329-333 (2004).

* cited by examiner

WOUND CARE PRODUCTS WITH PERACID COMPOSITIONS

CROSS-REFERENCE TO RELATED APPLICATIONS

This application is a Continuation-in-Part of U.S. patent application Ser. No. 13/400,013, filed Feb. 17, 2012, entitled "Compositions Comprising Peroxy alpha-Ketocarboxylic Acid and Methods for Producing and Using the Same", which application claims the benefit of U.S. Provisional Application Ser. No. 61/444,111, filed Feb. 17, 2011 and U.S. Provisional Application Ser. No. 61/565,986, filed Dec. 2, 2011. This application also claims the priority benefit U.S. Provisional Application Ser. Nos. 61/683,054, filed Aug. 14, 2012, 61/693,009, filed Aug. 24, 2012, and 61/715,725, filed Oct. 18, 2012, all of which are incorporated herein by reference in their entirety.

FIELD OF THE INVENTION

This present invention relates to wound coverings, dressings, and bandages and other matrices impregnated with or attached to peracid compositions.

BACKGROUND OF THE INVENTION

Depending upon the severity of the wound, the proliferative phase and final maturation of the wound to complete scar tissue can take from days up to years. Wound healing utilizes an extremely complex array of integrated biochemical events involving a regulated cascade of inter and intra cellular events. The biochemical response at the cellular level is a process involving intricate interactions among different cell functions, which include energy production, structural proteins, wound healing growth factors, proteinases, and microbial removal. Once a wound occurs, each of these cellular functions is critical to the healing process. If infection or other wound antagonists are encountered, then there is a delay in the wound healing and subsequent consequences which can be fatal. In addition, depending upon the physical condition of the patient, chronic wounds can develop which may take years to heal and lead to significant morbidity and treatment costs. Therefore, obstruction to any phase of the wound healing process can lead to complications and possible formation of a chronic wound, long term hospital stay with increased risk of a nosocomial infection, disability, and/or death. Currently, many treatment protocols for wound healing involve the use of molecular stimulators such as nucleotides, polysaccharides, and/or proteins (generally referred to as growth factors), and antioxidants. These cellular molecules function to incite cellular matrix formation, angiogenesis and other response(s) within the wound to enhance the healing process. In addition, different classes of drugs are applied to wounds such as hemostatic drugs, anti-inflammatory drugs, analgesic drugs, and angiogenesis drugs.

However, since there are numerous metabolic events that occur during the wound healing processes, it is generally believed that none of these conventional wound healing methods are an all en-compassing solution to efficient and safe wound healing. In addition, these wound healing compounds do not address the problem of infection control. Some of the limitations for many of these conventional wound healing treatments are the inability to efficiently deliver these compounds to deep wound cells involved in wound healing, inability to address the problem of infection control with sanitizers and/or antibiotics, and/or cost justification for affordable treatment plans.

Today's primary therapy for wound infection involves the use of either topical application of antiseptics and/or systemic and topical use of antibiotics. The general perspective is that topical application of antibiotics to wounds has no advantages over the use of other antiseptic methods and may increase the risk of delayed wound-healing by producing a sovereign bacterium that is resistant within the wound. Silver based dressings for treatment of infections is widely used in wound treatments. There are several of these commercially available such as Acticoatt™, Aquacels Ag®, Contreet® Foam, PolyMem® Silver, Urgotul® SSD. Unfortunately, these silver containing dressings do not kill spores or biofilms and require long exposure times that may result in cytotoxicity to the patient's own cells. The cytotoxic effect explains, in part, the clinical observation of delayed wound healing or inhibition of wound epithelialization after the use of certain topical silver dressings. Other widely used sanitizers are chlorhexidine, Betadine, which is a compound of various compounds including iodine, polyhexanide (Prontosan®), hydrogen peroxide, as well as others. All of these compounds are known to be toxic to the healthy cells in and around the wound when used extensively. In addition, these anti-disinfectants have potential efficacy restrictions and can be counter productive to wound healing due to the cellular toxicity.

It is well known that infection is the number one variable to cause wound healing complications and subsequent dire medical consequences to the patient. With the rising number of cases of drug resistant sepsis infections, there is an urgent need for a composition that can effectively treat drug resistant sepsis infection without cytotoxicity to the cells and be applied in different matrices. A somewhat new practice for treating wound infections involves delivery of antibiotic drug compounds in some form of bandage or dressing. The wound healing advantages include the ability of the solid bandage matrices to provide protection while allowing oxygen penetration and moisture influx to the wound. However, continued exposure of the bandages/dressings in combination with the current antibiotics and antiseptics for disinfection lends itself to cytotoxicity and allergic reactions in the patient. Therefore, the ultimate need is an application using a combinational bandage with the wound healing advantages of the bandage/dressing material with a synergistic additive which is both antimicrobial and hastens wound healing without cytotoxicity.

The peracid compounds are prepared as a composition in an aqueous phase whereby they exist in equilibrium with the coordinated oxidizer. The peracid compounds present in this composition are however susceptible to degradation and loss of activity with dilution and long term exposure to water. This presents a formulation challenge for incorporating peracid compounds into aqueous bandages/dressings such as hydrogels and other aqueous wound treatment matrices.

SUMMARY OF THE INVENTION

Methods have been developed for incorporation of a peracid compound into or on wound application matrices, such as bandages or dressings, and other matrices which will favorably impact wound healing and help eliminate microbial infection. The peracid compound comprises a base compound that is metabolically pertinent to wound healing, the oxidized form of the base compound (a peracid), and an appropriate oxidizer, such as hydrogen peroxide. In addition, other excipients with wound healing potential, such as esters of the base compound, may be added to the peracid compound. The combination peracid-wound application matrices can be used to disinfect and heal various wound types with designed time release of the peracid compound.

In one embodiment, a wound treating matrix comprises one layer which is non-aqueous that comprises an antimicrobial composition comprising a carboxylic card, the peracid of the carboxylic acid, and an oxidizer in a non-aqueous medium. In another embodiment, a method of treating a wound comprises providing the wound treating matrix and topically applying it to the wound. In another embodiment, a wound treating matrix comprises one non-aqueous layer comprising a peracid composition and one layer comprising a wound treating agent. In another embodiment, a wound treating matrix comprises a wound treating agent and a peracid composition, wherein the peracid composition is encapsulated in a biocompatible structure. In another embodiment, a wound treating matrix comprises a polymer and a peracid, wherein the peracid is chemically bonded to the polymer.

DETAILED DESCRIPTION OF THE INVENTION

Figure 1:
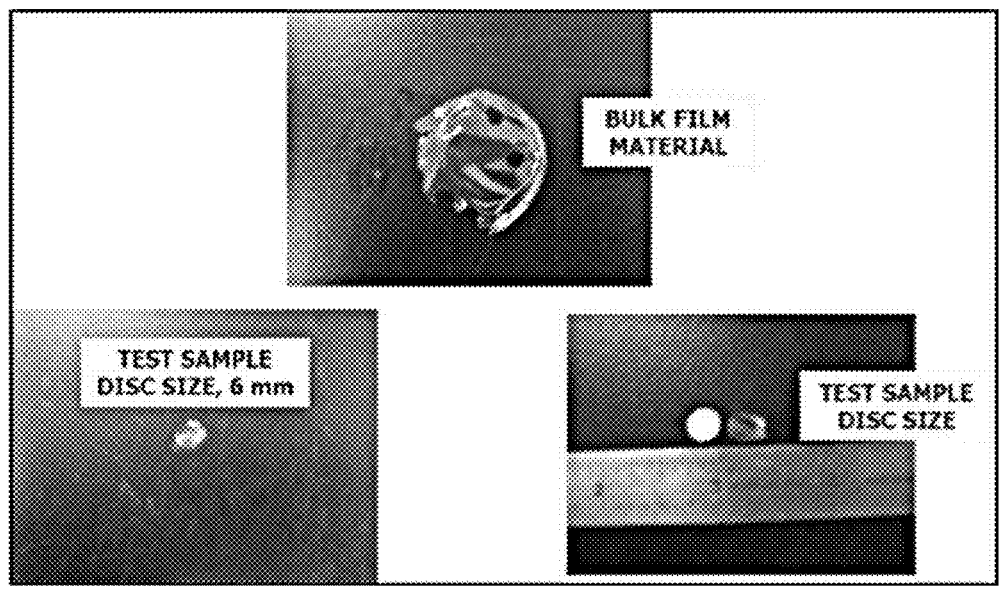
FIG. 1 shows dissolvable film impregnated with a peroxy pyruvic acid (PPA) compound and a control film without a PPA compound.

Currently, there is no sufficiently suitable composition that is available for treating a wound with both an effective broad spectrum antimicrobial activity and effective enhanced healing property. A chemical entity that has antimicrobial activity and is not susceptible to microbial resistance is a peracid synthesized by the reaction of an oxidizer with a carboxylic acid.

A wound disinfecting peracid composition that also enhances wound healing may be prepared by the reaction of an organic acid with an oxidizer where both the product of the reaction and the oxidizer are known to enhance wound cellular activity and signal a positive immune system response.

In one embodiment, peracid compounds or compositions containing peracid compounds are incorporated into a wound covering, dressing or bandage (collectively wound covering) that excludes water and is capable of delivering the composition to a wound. The product would be applied to acute and chronic wounds to aid in the debridement, disinfection and healing of wounds.

This combination treatment media of peracid in an appropriate application matrix will provide a beneficial aqueous environment and oxygen permeability for the wound and effectively release the peracid compound to the wound.

In one embodiment, appropriate peracid compounds are incorporated into a non-aqueous component of wound treatment materials that also have desirable characteristics of traditional wound coverings. Some example treatment materials would be hydrogel bandages/dressings, synthetic fiber bandages, flowable and non-flowable gels, sponges, creams and pastes that would be formulated using colloids, liposomes, micells, carbon nanostructures, and polymeric films. The chosen formulations would stabilize the peracid compound and maintain the efficacy and stability of the peracid compound.

The peracid wound treatment composition will be combined with the wound treatment material to form a wound application matrix which has important wound healing characteristics such as moisture and oxygen breathing capability. This combination of the peracid composition and the appropriate wound application matrix will provide the characteristics needed for debridement, disinfection, and wound healing. In addition, this wound covering, which is the peracid composition/application matrix combination, will be able to continuously release the disinfectant and control pH throughout the course of the wound healing and regenerative processes.

In one embodiment, the peracid compound/application matrix would be used for preventative disinfection of traumatic wounds by early release of the peracid compound. Afterwards, an application matrix would be applied that allowed for the slow release of the peracid compound for continuous anti-septic treatment.

Forms of wound application materials and matrices/designs for treatment of wounds include natural and synthetic fiber bandages, films, flowable and non-flowable gels, sponges, creams and pastes, colloids, etc. An ideal wound application removes excess exudate, maintains a moist environment, destroys and protects against microbial contaminants, allows oxygen permeability, does not cause damage to healthy cells and induces no allergic reactions. These wound healing applications may or may not include organic or inorganic compounds having antimicrobial properties, and/or biological preparations such as structural proteins, and fibrin. A wound application matrix which contains a superior antimicrobial compound which is not susceptible to antibiotic resistance is greatly desired. An added benefit of a combination antimicrobial/healing compound to a wound application matrix, e.g. a dressing and/or bandage, would be the ability to disinfect and destroy biofilms by a designed time release of the pro-healing/antimicrobial.

One embodiment provides a wound covering that releases a peracid composition to the wound over time. An example is a dissolving film comprised of the peracid that is capable of releasing the peracid to the wound.

A dissolving film layer for use in bandages/dressings, etc. may optionally comprise in part or in whole a hydrocolloid. Preferably, the hydrocolloid comprises a water soluble natural polysaccharide or derivatives including pectin and derivatives, guar gum arabic, tragacanth gum, xanthan gum, gellan sodium salt, propyleneglycol alginate, starches (amylose, amylopectin), modified starches, hydroxyethyl starch, pullulan, carboxymethyl starch, gum ghatti, okra gum, karaya gum, dextrans, dextrins and maltodextrins, konjac, acemannan from aloe, locust bean gum, tara gum, quince seed gum, fenugreek seed gum, scleroglucan, gum arabic, psyllium seed gum, tamarind gum, oat gum, quince seed gum, carrageenans, scleraglucan, succinoglucan, larch arabinogalactan, flaxseed gum, chondroitin sulfates, hyaluronic acid, curdlan, chitosan, deacetylated konjac, and rhizobium gum.

The hydrocolloid may be a water soluble non-gelling polypeptide or protein exemplified by gelatins, albumins, milk proteins, soy protein, and whey proteins. The hydrocolloid further may be selected from a group of synthetic hydrocolloids exemplified by polyethylene-imine, hydroxyethyl cellulose, sodium carboxymethyl cellulose, carboxymethyl cellulose, hydroxypropyl cellulose, hydroxypropyl methyl cellulose, methyl cellulose, ethyl cellulose, polyacrylic acids, low molecular weight polyacrylamides and their sodium salts (carbomers), polyvinylpyrollidone, polyethylene glycols, polyethylene oxides, polyvinyl alcohols, pluronics, tetronics, and other block co-polymers, carboxyvinyl polymers, and colloidal silicon dioxide.

Suitable hydrocolloids or mixtures producing synergistic properties comprise natural seaweeds, natural seed gums, natural plant exudates, natural fruit extracts, biosynthetic gums, gelatines, biosynthetic processed starch or cellulosic materials, alginates, agar gum, guar gum, locust bean gum (carob), carrageenan, tara gum, gum arabic, ghatti gum, Khaya grandifolia gum, tragacanth gum, karaya gum, pectin, arabian (araban), xanthan, gellan, starch, Konjac mannan, galactomannan, funoran, are xanthan, acetan, gellan, welan, rhamsan, furcelleran, succinoglycan, scleroglycan, schizophyllan, tamarind gum, curdlan, pullulan, and dextran.

Additionally, the dissolving layer may comprise any or all of emulsifying agents, solubilizing agents, wetting agents, taste modifying agents, plasticizers, active agents, water soluble inert fillers, preservatives, buffering agents, coloring agents, and stabilizers. Addition of a plasticizer to the formulation can improve flexibility. The plasticizer or mixture of plasticizers may be polyethylene glycol, glycerol, sorbitol, sucrose, corn syrup, fructose, dioctyl-sodium sulfosuccinate, triethyl citrate, tributyl citrate, 1,2-propylenglycol, mono-, di- or triacetates of glycerol, or natural gums. Preferred plasticizers are glycerol, polyethylene glycol, propylene glycol, citrates and their combinations. The amount of plasticizer depends on the final application.

Examples of natural water-soluble polymer include plant-type polymer, microorganism-type polymers and animal-type polymers. A plant-type polymer may be gum arabic, gum tragacanth, galactan, guar gum, carob gum, karaya gum, carrageenan, pectin, agar, quince seed or *Cydonia oblonga*, algae colloids such as brown algae extract, starches such as rice, corn, potato, and wheat, and glycyrrhizic acid. Microorganism-type polymers may be xanthan gum, dextran, succinoglucan, and pullulan. Animal-type polymers may be collagen, casein, albumin, and gelatin.

The water soluble polymer may further be selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof.

The film-forming agent used in the films can be selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof. The film may be formed from pullulan, in amounts ranging from about 0.01 to about 99 wt. %, preferably about 30 to about 80 wt. %, more preferably from about 45 to about 70 wt. % of the film and even more preferably from about 60 to about 65 wt. % of the film.

Examples of the semisynthetic water-soluble polymers include starch-type polymers, cellulosic polymers and alginic acid-type polymers. Starch-type polymers may be carboxymethyl starch and methylhydroxypropyl starch. Cellulosic polymers may be methyl cellulose, ethyl cellulose, methylhydroxypropyl cellulose, hydroxyethyl cellulose, cellulose sodium sulfate, hydroxypropyl cellulose, carboxymethylcellulose, sodium carboxymethyl cellulose, crystal cellulose, and cellulose powder. Alginic acid-type polymers may be sodium alginate and\ propyleneglycol-alginate.

Examples of the synthetic water-soluble polymers include vinyl polymers, polyoxyethylene-type polymers, acrylic polymers, and cationic polymers, and polyethyleneimine. Vinyl polymers may be polyvinyl alcohol, polyvinyl methyl ether, polyvinylpyrrolidone, carboxy vinyl polymer. Polyoxyethylene-type polymers may be a copolymer of polyethylene glycol 20,000, 40,000, or 60,000 and polyoxyethylene polyoxypropylene. Acrylic polymers may be sodium polyacrylate, polyethylacrylate, and polyacrylamide.

Thickeners may include gum arabic, carrageenan, karaya gum, gum tragacanth, carob gum, quince seed or *Cydonia oblonga*, casein, dextrin, gelatin, sodium pectate, sodium alginate, methyl cellulose, ethyl cellulose, CMC, hydroxy ethyl cellulose, hydroxypropyl cellulose, PVA, PVM, PVP, sodium polyacrylate, carboxy vinyl polymer, locust bean gum, guar gum, tamarind gum, cellulose dialkyl dimethylammonium sulfate, xanthan gum, aluminum magnesium silicate, bentonite, hectorite, AlMg silicate or beagum, laponite, and silicic acid anhydride. Preferred thickening agents include methylcellulose, carboxyl methylcellulose, and the like, in amounts ranging from about 0 to about 20 wt. %, preferably about 0.01 to about 5 wt. %.

Preferred surfactants include mono and diglycerides of fatty acids and polyoxyethylene sorbitol esters, such as, Atmos 300 and Polysorbate 80. The surfactant can be added in amounts ranging from about 0.5 to about 15 wt. %, preferably about 1 to about 5 wt. % of the film. Other suitable surfactants include pluronic acid, sodium lauryl sulfate, and the like.

Preferred stabilizing agents include xanthan gum, locust bean gum and carrageenan, in amounts ranging from about 0 to about 10 wt. %, preferably about 0.1 to about 2 wt. % of the film. Other suitable stabilizing agents include guar gum and the like. A number of naturally occurring small organic molecules display chaperone-like activity, stabilizing the native conformation of proteins. Most of them are sugars, polyols, amino acids or methylamines. For example, the capacity of trehalose and glycerol, to stabilize and renature cellular proteins is well known.

Preferred emulsifying agents include triethanolamine stearate, quaternary ammonium compounds, acacia, gelatin, lecithin, bentonite, veegum, and the like, in amounts ranging from about 0 to about 5 wt. %, preferably about 0.01 to about 0.7 wt. % of the film. Preferred binding agents include starch, in amounts ranging from about 0 to about 10 wt. %, preferably about 0.01 to about 2 wt. % of the film. It may be necessary to additionally incorporate compounds that act as preservatives or buffers. An example of such a material is sodium benzoate.

By choosing the physical properties of the dissolving layer, it is possible to control the delivery of the active material to the tissue. For example, the size (area, $cm^2$) of the dissolving layer in contact with the tissue determines the dose rate (mg/hr.) and the total amount (mg) of active material delivered. The flux (mg/hr./cm2) is a property that is important to consider; for example, particular active materials are toxic to the tissue at critical dose intensities (gm/cm2). To reduce local toxicity, and to increase dose rate, it may be beneficial to increase the area of the dissolving layer that is in contact with the tissue.

A thicker dissolving layer, or a dissolving layer formulated with certain excipients (e.g. hydroxypropylcellulose) which inhibit dissolution, can be used to control the rate at which the active material is delivered from the matrix. Other excipients include: (1) carboxymethyl cellulose (CMC) which is a viscosity thickener, emulsion stabilizer. It is notable in that its non-polar methyl groups do not add any solubility of chemical reactivity to the base cellulose (unlike methyl cellulose); (2) hydroxypropyl cellulose (HPC) which is a viscosity thickener, disintegrant, binder, emulsion stabilizer and soluble in water up to about 45° C.; (3) methyl cellulose (MC) which is a viscosity thickener, disintegrant, binder, emulsion stabilizer and dissolves in cold water (40-50° C.) and gels in hot (when a saturated solution) because it precipitates out; (4) ethyl cellulose (EC) which is a solvent free coating that creates semi-permeable membranes for drugs to pass-diffusion-controlled rate limiter; (5) hydroxypropyl methylcellose (HPMC) which is a viscosity thickener, binder, emulsifier, stabilizer and nonionic water soluble, pseudoplastic in aqueous solution and reversibly gels in hot water; critical temperature inversely related to the concentration of HPMC and the degree of substitution of the methoxy group; (6) 2-hydroxyethyl cellulose (HEC) which is a viscosity thickener, disintegrant, binder, emulsion stabilizer that is nonionic water soluble, pseudoplastic in aqueous solutions; (7) guar gum which is a nonionic polysaccharide; thickener and stabilizer, disintegrant, emulsifier. Borax (sodium borate) or Ca (for example, calcium chloride), or can cross-link to cause it to gel; (8) xanthan gum which is a polysaccharide; thickener and stabilizer; (9) carrageenan which is a polysaccharide; gelling, thickening and stabilizing. k-carrageenen is sometimes used for drug encapsulation, i-carrageenen gives an elastic medium strength gel and 1-carrageenen is non-gelling; (10) alginate (along with sodium and calcium alginate) which is an anionic polysaccharide distributed widely in the cell walls of brown algae, where it, through binding water, forms a viscous gum. In extracted form it absorbs water quickly; it is capable of absorbing 200-300 times its own weight in water, and can increase gel strength and decrease drug release; (11) polyethylene glycol (PEG) which is an oligomer of ethylene oxide of various molecular weights and is ubiquitous in the pharmaceutical industry as a dispersant, thickener, filler, lubricant, and plasticizer; and (12) glycerol which is a water-soluble viscous liquid used in many pharmaceuticals mainly for improving lubrication or as a humectant and for enhancing the viscosity of aqueous solutions.

One embodiment provides a wound dressing with at least two layers whereby one layer is a stabilizing matrix, and the second layer is a drug eluting matrix. Another embodiment provides a time release matrix comprised of the peracid composition that is capable of releasing the composition to the wound over a period of time where the time release matrix may be, but is not limited to, a hydrogel or fast dissolving film.

Another embodiment provides a multi-layer system comprised minimally of a hydrogel in combination with a dissolving film, or other means of releasing the peracid composition to the hydrogel, where the hydrogel composition modulates the rate of release of the peracid to the wound.

Another embodiment maintains the peracid composition in a non-aqueous matrix, and exposing it to an aqueous component just prior to or during application. One embodiment provides a combination of hydrogel and dissolving film matrix whereby the dissolving film is separated from the hydrogel by a fluid resistant barrier. In one embodiment, the fluid resistant barrier is removable, and once removed, allows moisture from the hydrogel to dissolve the film.

In one embodiment, the fluid resistant barrier is a thin film that separates the hydrogel from the dissolving film. In another embodiment, the wound patch includes a reservoir, which may be filled with an aqueous solution, which bursts with pressure.

Another embodiment provides a system, which is a multi-layer wound covering, where two or more layers that comprise the system are assembled just prior to application. For example, the peracid composition may comprise a dissolving film, which may be applied to a moist matrix, such as a hydrogel, just prior to application to the wound.

One embodiment provides a system whereby a dissolving film matrix is combined with a drug eluting medium to deliver a peracid composition to a wound.

One embodiment provides means to maintain the peracid composition in a non-aqueous medium include beads, films, powders or gels. The non-aqueous medium may be dissolvable or biodegradable. In another embodiment, the eluting matrix may be dry, and hydrated prior to use. Another embodiment provides the delivery of a controlled dosage of a peracid composition to the wound.

One embodiment provides a drug-delivery matrix incorporating at least one dissolving component for use in treating compromised skin, including skin wounds, whereby a layer which is proximal to the wound, or in contact with the wound, dissolves upon contact with fluids expressed from the wound, thereby releasing an active ingredient into the wound.

In general, peracids are compounds of oxidized form of a base organic acid (generally a carboxylic acid) that exist in equilibrium with an oxidizer (generally hydrogen peroxide) and water, as shown in scheme 1. One species of peracid with superior antimicrobial properties are peroxy alpha-keto acid (PKCA) compounds (see U.S. Patent Application Publication No. 2010/0261792). PKCA compounds would generally be composed of an alpha-keto carboxylic acid, the anion of that alpha-keto acid, a buffer, and hydrogen peroxide, and the oxidized form of the carboxylic acid. A peroxy pyruvate acid (PPA), for example, may be in equilibrium with pyruvic acid, acetic acid and peracetic acid, as shown in scheme 2. Peracids may be oxidized from other carboxylic acids, e.g. citric acid, succinic acid, short chain fatty acids, and etc. It can be recognized that other carboxylic acids involved in cellular metabolism, e.g. citric acid, succinic acid, short chain fatty acids, and etc. can be used to produce wound treatment peracid compounds.

Scheme 1

Scheme 2

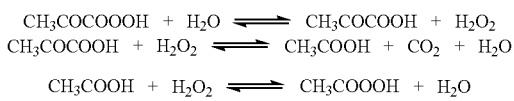

As an example of a wound healing peracid compound, pyruvic acid could be the base alpha-keto acid, and the compound would include the anion of pyruvic acid, hydrogen peroxide, and the peroxy pyruvic acid (PPA). Pyruvic acid is metabolically used in cellular metabolism to produce carbohydrates via gluconeogenesis, fatty acids, and the amino acid, alanine. In addition, pyruvate in anion form is the primary molecule metabolized for cellular energy production through the TCA cycle. The PPA of the peracid compound is an oxidizer in the oxidative category of hydrogen peroxide or hypochlorite. Therefore, the PPA compound as an antimicrobial will kill the wound infection due to the oxidative denaturation of the bacterial proteins, enzymes and cell wall and membrane components. The $H_2O_2$ as the carboxylic acid oxidizer is in equilibrium with the pyruvic acid and PPA compound. The oxidizer, hydrogen peroxide is also involved in metabolic signaling necessary for wound healing.

Pyruvic acid is the simplest of all the alpha-keto acids and, as mentioned, the base for the formation of the PPA compound. The use of pyruvic acid in the process of wound healing first occurred in 1946 to treat burn wounds. The treatment resulted in rapid deterioration of the injured cells (slough/chemical debridement) before subsequent surgical debridement. In addition, the pyruvic acid application demonstrated favorable growth of the surviving cells within the slough area. This application was an early demonstration of the potential use of alpha-keto acids, in particular pyruvic acid for wound healing. Today, pyruvic acid is used in the treatment of acne, which is a form of chronic wound. In the treatment of acne, pyruvic acid not only kills the microbial infection but acts as a humectant and inhibits dehydration of the cells. It is well known that pyruvate is involved in critical metabolic processes required in cells. There is strong evidence which suggests that the external application of pyruvate anions are relevant metabolic determinants in PMN nutrition and thus affect the magnitude and quality of the granulocytic host defense response. In addition, oxygen demand (known as hypoxia) in wounds exceeds supply for a few days following injury. Pyruvate is the primary source of energy for hypoxic cells through the anaerobic pathway of glycolysis and oxidative glycolysis which may play a role in pyruvate reducing DNA damage during hypoxia. Pyruvate in hypoxic cells becomes an indirect metabolic contributor to other cellular functions through lactate signaling for collagen deposition and angiogenesis in wound healing. Finally, pyruvate and lactate together play a role in the up regulation of the angiogenic factor vascular endothelial growth factor (VEGF).

As indicated above, the oxidizer $H_2O_2$ is in equilibrium with pyruvic acid in the peracid compound. Cytotoxic oxidizers, such as hydrogen peroxide, are released by cells in the inflammatory phase of a wound and are known as the Reactive Oxygen Species (ROS). When these reactive species are successful in killing the wound microbial contamination, then the wound is able to close and heal. However, if the ROS released at the inflammatory phase remains too long in the wound due to persistent inflammation from microbial colonization, these oxidizers can become toxic to the healthy cells. Of all the ROS oxidizers, $H_2O_2$ and only $H_2O_2$, has a long enough half-life to accumulate in the culture medium of cells. Recent research indicates that there is a reason for this. It has been demonstrated that $H_2O_2$ stimulates human macrophages to release high levels of vascular endothelial growth factor a known stimulator of angiogenesis. It has also been shown that hydrogen peroxide stimulates re-epithelization of wounds, wound coagulation of neutrophils, and monocyte adhesion to the extracellular matrix and endothelial cells. In addition, hydrogen peroxide, as a messenger stimulates growth factors required for wound healing such as platelet derived growth factor (PDGF), tissue growth factor (TGF), epidermal growth factor (EGF). However, the continuous addition of high levels of $H_2O_2$ to diminish microbial infection is known to be toxic to cells and therefore not recommended. In contrast, recent discoveries suggest that the metabolic signaling mechanisms of $H_2O_2$ present in micromolar concentrations per gram of tissue are significantly involved in wound healing and $H_2O_2$ is being called the new star in wound healing. The concentration of $H_2O_2$ in a peracid compound used for wound healing and disinfection will contain the optimal micro molar per gram of tissue concentration.

In addition to the base organic acid, the oxidized acid, and the oxidizer, other excipients can be added to a peracid compound to help enhance wound healing. These include different classes of drugs such as hemostatic drugs, anti-inflammatory drugs, analgesic drugs, and angiogenesis drugs. Examples of hemostatic drugs include aminocparoic acid and tranexamic acid. Examples of anti-inflammatory drugs are NSAIDs, steroids, paracetamol, prostaglandins, and etc. Examples of analgesic drugs are Acetaminophen, Morphine, Codeine, Hydrocodone, Tramadol, Opioids, and Salcilic acid. Examples of angiogenesis drugs are Angiogenin, Fibroblast Growth Factor, VEGF, PDGF, Insulin-like Growth Factor. The ethyl ester of pyruvic acid has been shown to be an anti-inflammatory and can be added to the PPA composition as such. Other esters of the base organic acid in peracids can be used as well.

Peracid compounds incorporated into wound application matrices provides a therapeutic method for treatment of traumatic, burn, and chronic wounds. The combination peracid compound-wound application matrices provide wound disinfection without microbial resistance, debridement, and enhanced wound healing. In addition, the combination peracid-wound application matrices, e.g. a dressing and/or bandage, can be used to disinfect and destroy biofilms in chronic wounds and pressure ulcers with a designed time release of the peracid compound.

In one embodiment, the chemical and anti-microbial activity of peracids and peracid-containing compositions may be stabilized in the dissolvable film containing peracids. Generally, the peracid may be impregnated, suspended in, or attached to a non-aqueous medium, and stored for extended periods while retaining chemical and antimicrobial activity.

Examples of non-aqueous media that may be capable of stabilizing peracids and peracid compositions include films, powders, gels, meshes, colloids, liposomes, micelles, or carbon nanostructures.

In some embodiments, the non-aqueous medium comprises polymers derived from plants, microorganisms or animals, microorganism-type polymers and animal-type polymers. A plant-derived polymer may be gum arabic, gum tragacanth, galactan, guar gum, carob gum, karaya gum, carrageenan, pectin, agar, quince seed or *Cydonia oblonga*, algae colloids such as brown algae extract, starches such as rice, corn, potato, and wheat, and glycyrrhizic acid. A microorganism-derived polymers may be xanthan gum, dextran, succinoglucan, and pullulan. Animal-derived polymers may be collagen, casein, albumin, and gelatin.

In some embodiments, the film-forming agent used in the films can be selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof.

One embodiment provides a dissolvable film comprised of a complex polysaccharide, such as pullulan, along with a plasticizer, such as lambda carageenan.

The non-aqueous media may optionally comprise in part or in whole a hydrocolloid. In some embodiments, the hydrocolloid comprises a water soluble natural polysaccharide or derivatives including pectin and derivatives, guar gum arabic, tragacanth gum, xanthan gum, gellan sodium salt, propyleneglycol alginate, starches (amylose, amylopectin), modified starches, hydroxyethyl starch, pullulan, carboxymethyl starch, gum ghatti, okra gum, karaya gum, dextrans, dextrins and maltodextrins, konjac, acemannan from aloe, locust bean gum, tara gum, quince seed gum, fenugreek seed gum, scleroglucan, gum arabic, psyllium seed gum, tamarind gum, oat gum, quince seed gum, carrageenans, scleraglucan, succinoglucan, larch arabinogalactan, flaxseed gum, chondroitin sulfates, hyaluronic acid, curdlan, chitosan, deacetylated konjac, and rhizobium gum.

The non-aqueous peracid composition may be stored at room temperature or, in a refrigerator, preferable in a light-tight container as the material can photodegrade in the presence of light, especially ultraviolet. The non-aqueous peracid composition is stable after a long period of time. Long term storage stability refers to the non-aqueous peracid composition's retaining their chemical activity over extended periods of time, e.g. over twelve months. In one embodiment, the composition provides non-aqueous peracids that exhibit unusually good storage stability retaining at least 60% of the initial peracid concentration for at least twelve months.

The peracid compositions have wide applicability as a disinfecting, sterilizing, biocidal or antimicrobial agent in both commercial and consumer applications. Commercial or industrial applications include the food processing, beverage, pharmaceutical and medical industries, industrial waste water, and use as a bleaching agent in the textile, pulp and paper industries. Consumer applications include laundry and bleaching uses.

In some embodiments, it is desirable to remove the film polymer just prior to or during application of peracids. The polymer dissolves upon contact with fluids, thereby releasing peracids. In one embodiment, the polymer may be separated from peracids by boronic acids prior to or during application of peracids.

As a carbohydrate polymer, pullulan may be removed from solution by a boronic acid modified resin. To create a carbohydrate-removal system, the capture resin would first be modified with a boronic acid. A wide range of resins would be appropriate ranging from silica to organic polymer in fundamental chemistry. The immobilization chemistry is also not specific but should allow linkage of the boronic acid species without altering the boronic acid functionality. In one embodiment, Toyopearl AF-Carboxy-650 resin particle is used as a resin, 1-ethyl-3-(3-dimethylamino-propyl)carbodiimide (EDC) as a cross-linking agent, and 4-aminophenylboronic acid as the capture agent. These three reagents can be mixed together in a water based synthesis protocol to yield boronic acid modified resin.

Once the resin is modified, it could be packed into a column format where sample containing carbohydrates would be pulled through the resin before being dispensed. In one embodiment, a small cartridge is loaded on the end of a tube that contains the resin. As liquid was pulled through the cartridge the carbohydrate would react with the boronic acid and become immobilized. The remaining solution would flow through the rest of the tube for dispensing.

In one embodiment, a stable composition comprises a non-aqueous medium containing a carboxylic acid, the peracid of the carboxylic acid, and oxidizer. In another embodiment, a composition comprises a dissolvable polymer, and a carboxylic acid, the peracid of the carboxylic acid, and an oxidizer impregnated in the dissolvable polymer. In another embodiment, a method of stabilizing a peracid compound comprises mixing the peracid compound with a dissolvable polymer in an aqueous solution, and drying the mixture to make a peracid-containing composition.

In another embodiment, a method for sterilizing, disinfecting, or sanitizing hard or porous surfaces, fabrics, or medical devices comprises dissolving the composition comprising a non-aqueous medium containing carboxylic acid, the peracid of the carboxylic acid, and oxidizer, separating the non-aqueous medium from the peracid, and applying the peracid on the surfaces, fabrics, or medical devices. In another embodiment, the peracid is applied on the surfaces, fabrics or medical devices without being separated from the non-aqueous medium.

As illustrated in FIG. 1, peracids can be incorporated into solid phase matrices and maintain stability. This bulk film material illustrated in the drawings can be easily fit between layers of dressing or gauze and protected from the moisture in the bandage. As shown in FIG. 1, a 100 ppm and 1000 ppm PPA compound were formulated into a solid phase matrix. To test efficacy and stability of the incorporated PPA compound, six millimeter discs were cut out of the PPA treated matrices and placed onto a methicillin resistant *staphylococcus aureus* (MRSA) streaked blood agar plate. A control film matrix disc which did not contain the PPA compound was prepared as well. This method simulated the well-known minimum inhibitory concentration (MIC) test. The blood agar plates were incubated overnight at optimal temperature and then observed for microbial kill.

Figure 2:
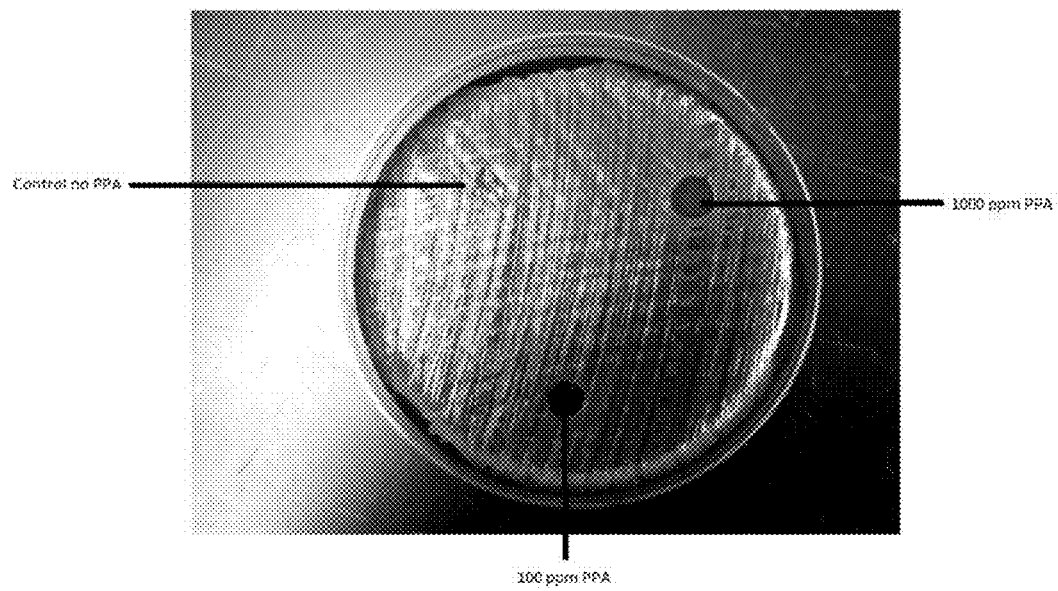
FIG. 2 shows treatment of MRSA on blood agar plate with PPA compound incorporated in dissolvable film.

As shown in FIG. 2, the blood agar plate was treated with the solid phase matrix discs containing the PPA compound at 100 ppm and 1000 ppm illustrated in FIG. 1 was observed for the diameter of bacteria kill the circle. The control film disc was the diameter of the grown of the 1000 ppm disc. The discs were placed on the blood agar plate and were dissolved by the moisture from the agar which allowed the PPA compound to migrate out of the film. The kill of MRSA was in proportion to the PPA concentration in the disc. Thus the 1000 ppm ratio of ppm concentration to the circle of kill diameter was greater than for the 100 ppm concentration to the circle diameter in millimeters. Calculations demonstrated that the proportionate diameters divided by the weight of the film was consistent with the expected concentrations.

Figure 3:
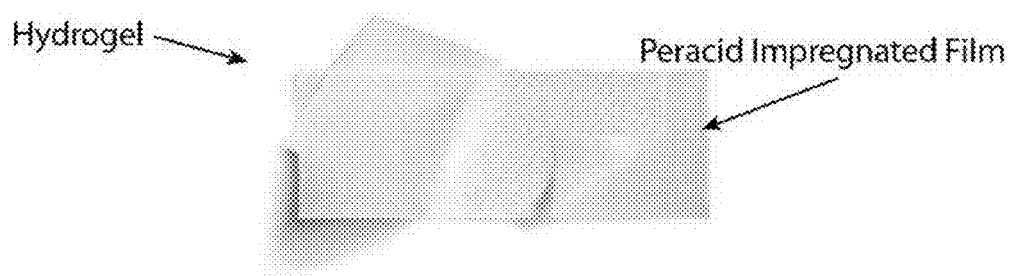
FIG. 3 shows a hydrogel dressing containing a peracid impregnated film.

As illustrated in FIG. 3, the bulk film material containing peracid may be incorporated as a layer in the hydrogel. One embodiment provides a hydrogel dressing with an impregnated peracid film (PIF) material as part of the dressing layers. The PIF material can be protected by another film which will be pulled out by the health care worker and then the wound/hydrogel moisture will dissolve the PIF material and release the Peracid compound into the wound.

Figure 4:
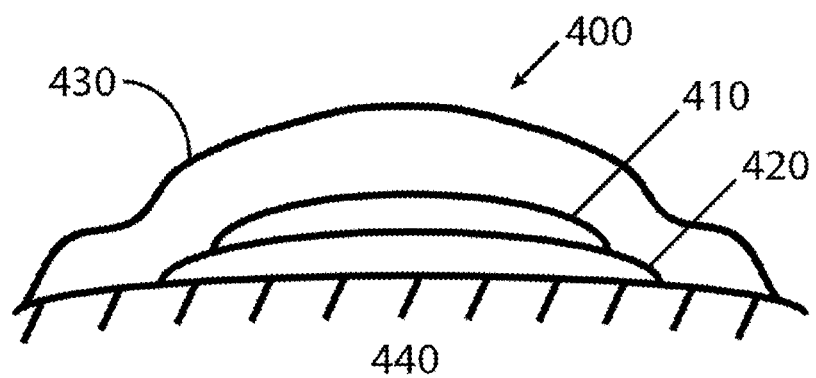
FIG. 4 shows a wound patch containing dissolving layer hydrogel-thin film combination.

FIG. 4 shows one embodiment of a wound treating matrix 400. In the embodiment, the active material is incorporated into an excipient that forms a dissolvable layer 410; this layer 410 may be solid or semi-solid. The layer 410 may be held in intimate contact with a hydrogel 420, all of which is protected by an adhesive backing or cover 430. The hydrogel serves to dissolve the layer 410 and allow permeation of the active ingredient from 410 through 420 into the skin 440. It also serves to maintain the moistness of the wound to which it is applied, and to conform to the irregular contours of a wound. Depending on the formulation of the dissolvable layer 410 and the hydrogel 420, the dissolution of layer 410 and/or permeation of the active ingredient in 410 through 420 into the wound on the skin 450 can be beneficially modified.

Figure 5:
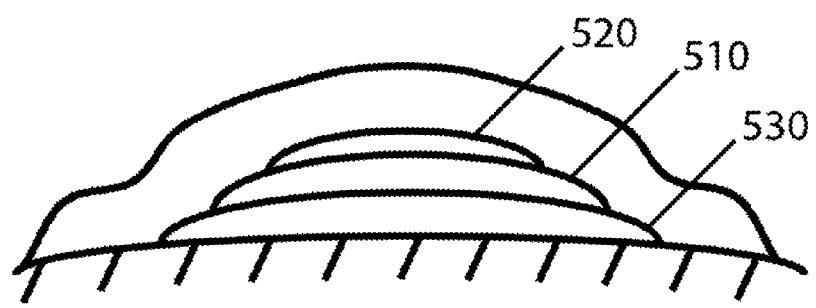
FIG. 5 shows a wound patch containing rate limiting dissolving layer.

As shown in FIG. 5, in another embodiment, there is an addition rate-limiting-membrane 510 positioned between the dissolvable layer 520 and hydrogel 530. This membrane 510 can be, for example, another hydrogel or a thin dry porous structure such as laboratory filter paper, for example, consisting of cellulose, carbon or quartz fibers, or semi-permeable membranes sometimes made up of nitrocelullose, track-etched polyester or polycarbonate, cellulose ester, polytetrafluoroethylene, polyimide, polysulfone, nylon, polyethersulfone, polypylene, aluminum oxide or ceramic. Many of these materials can be prepared as hydrophobic or hydrophillic, which also will affect the permeation (and potentially the retention) of the active ingredient.

Figure 6:
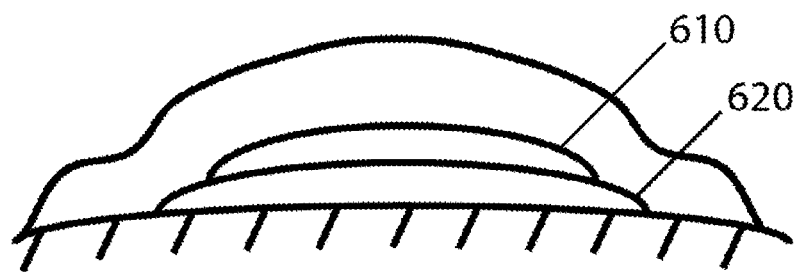
FIG. 6 shows a wound patch containing a permeable layer.

As shown in FIG. 6, in another embodiment, there are the dissolving layer 610 and a dry, flexible, permeable layer 620 made up of, for example, a thin permeable membrane such as cellulose or a hydrocolloid. The permeable membrane is thin enough to take up the irregular geometry of a wound, and in doing so, will allow permeation of interstitial fluid and exudate up into the dissolving layer 610, thereby releasing the active ingredient which will permeate down to the wound.

Figure 7:
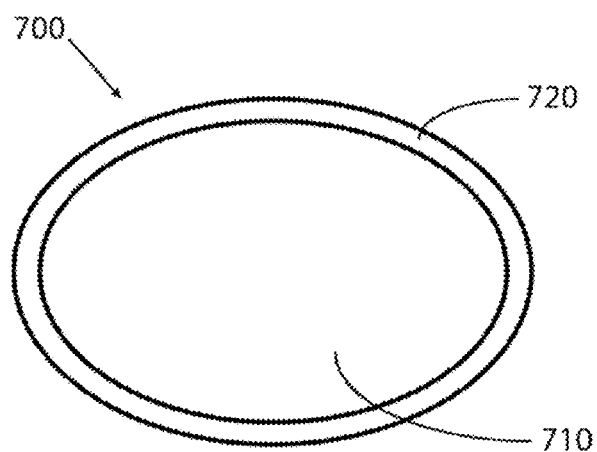
FIG. 7 shows film dissolution for direct application to wound.

FIG. 7 shows one embodiment of a dissolving structure 700. In the embodiment, the active ingredient 710, in dry form and thus stable, may be introduced into a solvent such as water whereby the dissolving membrane 720 allows the active ingredient to dissolve into water. This dissolving structure 700, which provides a stable environment for the active ingredient, is easily handled and shipped.

Figure 8:
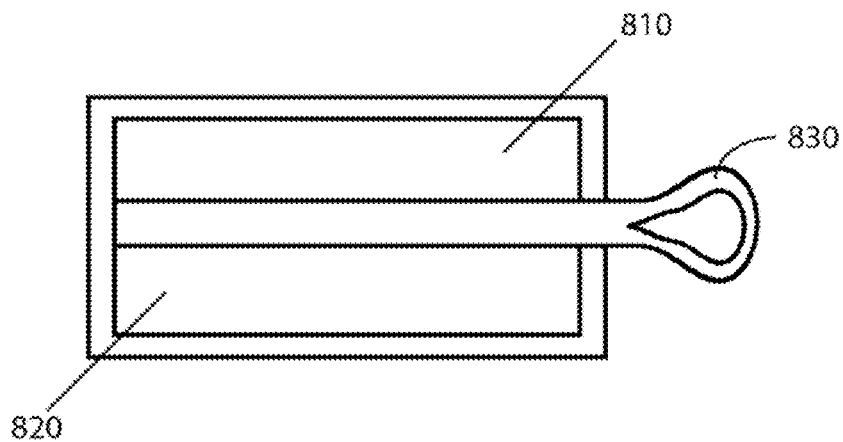
FIG. 8 shows cross-sectional view of a wound patch with a removable impermeable layer.

FIG. 8 shows one embodiment of a packaging arrangement whereby the moist hydrogel 820 is kept separate from the dissolving layer 810 until it is ready to be applied to the patient. At that time, the health-care provider allows the hydrogel 820 and dissolving layer 810 to join in intimate contact by removing an impermeable layer 830 that was positioned between the layers to prevent the movement of moisture into the dissolving layer. Alternatively, each components of the wound matrix could be packaged separately, and removed prior to application on the patient. Each component could then cut with scissors to conform to the shape of the wound or patient's anatomy, and then applied in order and covered with an occlusive or permeable dressing.

Figure 9:
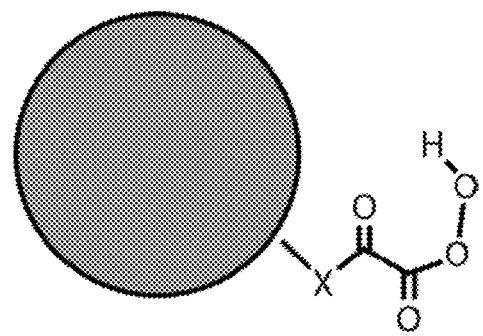
FIG. 9 shows one embodiment that peracid molecules are bound on a solid scaffold for wound treatment.

FIG. 9 shows one embodiment of a solid phase synthesis in which peracid molecules are bound on a solid scaffold, such as a resin, PVA, polyurethane, proteins, etc. These can be synthesized step-by-step in a reactant solution. Compared with normal synthesis which occurs completely in a liquid state, it is easier to remove excess reactant or byproduct from the product. One reactive group on the building blocks may react with one reactive group on the scaffold to chemically bond the building blocks and the scaffold. In this method, reactive functional groups other than the two reactive groups intended for the bonding reaction may be protected if necessary. For example, this method can be used for the synthesis of PPA on solid scaffolds.

In one embodiment, solid-phase of PPA is synthesized through combination of a solid scaffold (such as PVA or Polyurethane) which would have a functional group (i.e. hydroxyl), and a pyruvic acid derivative such as ethanedioic acid with one of the carboxylic acids shielded with a protecting group that can be cleaved later. The solid scaffold is added to an organic solution with the partially protected ethanedioic acid. Under the right conditions the ethanedioic acid couples to the solid scaffolds functional group by forming an ester linker, as an example. The solid scaffold with the coupled ethanedioic acid is then treated chemically to cleave the protecting group from the carboxylic acid. The resulting bound acid is then treated chemically to create the peroxy acid bound to the solid scaffold. The coupling to the scaffold could be a carbon molecule, an oxygen molecule, and etc. Afterwards, this scaffold can be used as a wound disinfectant.

Figure 15:
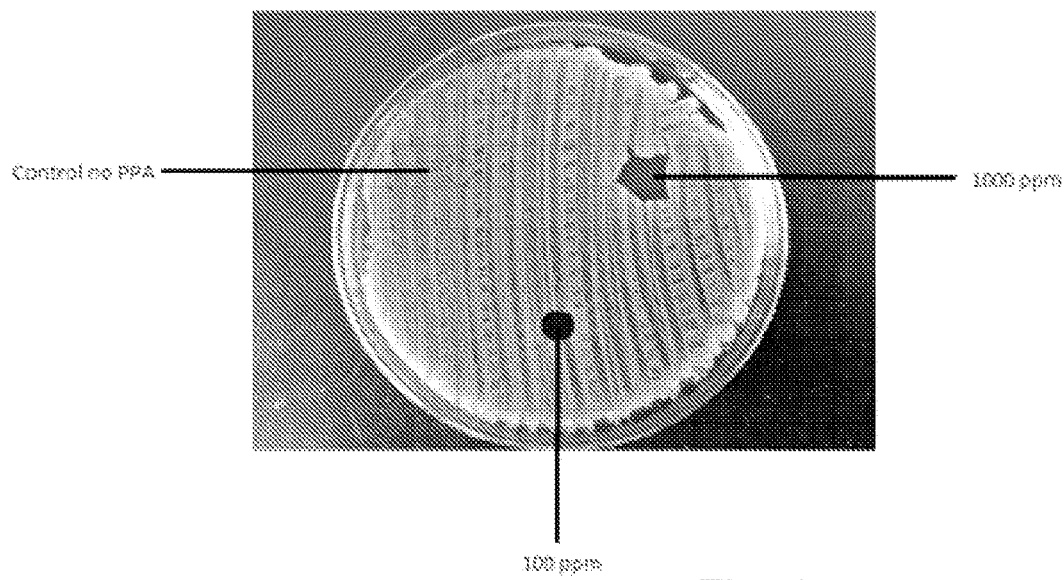
FIG. 15 shows treatment of MRSA on blood agar plate with PPA compound incorporated in dissolvable film after one year storage.

As shown in FIG. 15, the film containing PPA after one year storage still has chemical activity comparable to the newly made film.

Figure 16:
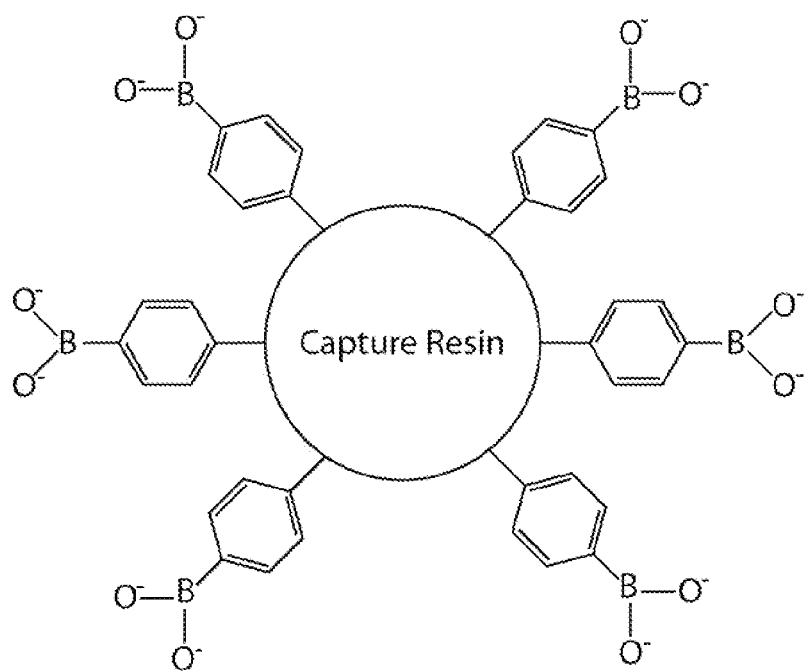
FIG. 16 shows solid phase capture resin modified with a phenyl boronic acid for removal of sugar residue.

As shown in FIG. 16, a polymeric resin may be modified with a phenyl-boronic acid derivative for separating pullulan from PPA.

EXAMPLES

Example 1

Dissolving Thin Film Formulation

In one embodiment, the film dissolves upon contact with a fluid, e.g., water from matrix such as a hydrogel, or fluids that are released from the treatment site.

The film may be comprised of a dissolvable hydrocolloid such as pullulan. The film may be comprised of one or more layers, any of which may be comprised further of an emulsifying agent, a solubilizing agent, a wetting agent, a taste modifying agent, a plasticizer, an active agent, a water soluble inert filler, a preservative, a buffering agent, a coloring agent, a stabilizer, or a combination thereof.

Formulations for the dissolvable layer may include: (1) fast-dissolving film component such as pullulan, generally 10-95% wt. %, (2) a plasticizer for flexibility such as λ-carrageenan, generally 0.05-35% wt. %, (3) a dissolution modulating agent (e.g. hydroxymethycellulose), generally 0.1%-10%, and (4) a surfactant, for dispersion, such as polysorbate A at 0.001-0.1%. The initial preparation is mixed in deionized water and cast. Final residual water content is generally 1-4% depending on method of casting and extent of drying.

An occlusive membrane, aluminized mylar, with an adhesive backing, or a semi-permeable membrane such as 3M Tegaderm, is typically applied over the matrix.

An example of an efficacious biocide matrix formulation is: the dissolvable layer is made up of (wt./wt.) 2.09% pullulan, 0.087% λ-carrageenan, 0.14% polysorbate A and 160 ml of deionized water. 9% biocide is added so that the concentration in the liquid biocide matrix is 100 to 10,000 ppm. The final biocide concentration in the dried matrixes can be about 44 times greater than the concentration in the liquid matrix prior to dry-down.

The liquid film material is cast on a Teflon plate or releasable membrane, such as silicone rubber, allowed to dry in a sterile tissue-culture hood for 4-24 hours. Thickness of the film is determined by composition, and is affected as well by final moisture content which is further affected by the extent of the drawdown. The thicknesses can vary widely, but can be, for example, from about 20 to 200 microns.

Example 2

Hydrogel—Dissolvable Film Multi-Layer Composition

A PVA hydrogel layer was prepared with 10% PVA (wt./wt.) mixed and heated at 95° C., allowed to cool, and then poured onto a glass plate with Teflon spacer (about 2.5 mm) to a size of 13×13×0.25 cm. Another glass plate was positioned on top and the two plates were clamped together with medium paper binder clips. The entire assembly was then wrapped in non-stick aluminum foil and subjected to one freeze-thaw cycle. In one embodiment, repeated cycles of freezing and thawing of polymer solution result in solids exclusion forcing polymer units in proximity with one another, probably through Van der Waals attractions, and possibly through ionic bonding, which leads to the generation of solid hydrogel. Preferably, the polymer is frozen at less than −20° C. for 10 to 20 hours, where cyclic freeze-thaws result in tighter bonding, which in turn allows one to vary the pore size in order to control the rates of dissolution of materials from the hydrogel, or the rate of permeation through the hydrogel.

Example 3

Preparation of a Thin Rapidly Dissolving Film

Formulations for the dissolvable layer may include: (1) Fast-dissolving film component such as pullulan, generally 10-95% wt. %, (2) a plasticizer for flexibility such as beta-carrageenan, generally 0.05-35% wt %, (3) a dissolution modulating agent (e.g. hydroxymethycellulose), generally 0.1%-10%, and (4) a surfactant, for dispersion, such as polysorbate A at 0.001-0.1%. The initial preparation is mixed in deionized water along with the peracid composition at its desired concentration (100 ppm to 10,000 ppm) and cast. Final residual water content is generally 1-4% depending on method of casting and extent of drying.

An occlusive membrane, aluminized mylar, with an adhesive backing is typically applied over the matrix.

The two components may be assembled just prior to application or while on the wound site whereby the dry film is applied to the top of the hydrogel which is placed in contact with the wound.

Alternatively, an occlusive film may be applied between the hydrogel and dry film layer such that the layer, or a portion of the layer, is removable. In one embodiment, the dry film is maintained as a dry component that is shielded from the moist hydrogel. When the occlusive layer is removed, aqueous solution permeates and dissolves the film, thus allowing the peracid composition to flow into the hydrogel and to the wound.

Example 4

Delivery of Biocide at Different Rates

The biocide is released from the dissolving layer upon disintegration and dissolution. The rate at which the film is dissolved or disintegrated provides an additional means of modulating the rate at which the peracid composition enters the matrix of the wound covering, which may be a hydrogel.

The disintegration and dissolving times are influenced by varying the film thickness t, or by varying the formulation of the film. For example, dissolving layer dissolution times (in water) varied from 0.5 minutes (t=30 μm) to 23.5 minutes (t=120 μm) in experimentation by adding hydroxypropylmethyl cellulose (HPMC; a cosmetic thickener and emulsifier) or hydroxymethylcellulose (HMC) to the formulation at a concentration of 0.125% w/w.

In another in vitro dissolution study, a 10×10 mm piece of the dissolving layer matrix was cut from the middle of sample matrixes, weighed, and the average thickness measured. Each sample was then immersed in a beaker of 200 ml deionized water and 0.0005% polysorbate-80, adjusted to pH=5.0 (like stratum corneum) and held at a constant temperature of 37° C. and stirred at ~200 rpm. At various times (5, 10, 15, 20, 30, 45, and 60 minutes) after matrix immersion, 1 ml samples of water were taken and tested spectrophotometrically for optical absorbance at the peak of the trypan blue dye absorbance. The area of the absorption peak was calculated and compared to the total amount of dye mixed in the matrix. These dissolution times, defined as the time that 85% of the dye was released from the sample matrix, were different for different dissolving layer thicknesses and concentrations of HPMC or HPC. Basically, the thicker the matrix, the longer it takes to dissolve, and the more HPMC or HPC in the matrix, the longer it takes to dissolve. Furthermore, it would be possible to make a bi-phasic matrix by laminating two different layers of dissolving layer matrix so that the layer in first contact with the ablated skin dissolves at a rate beneficial for the quick delivery of the biocide and quick microbe kill, after which the second layer comes into contact with the skin and delivers biocide at a slower rate to enhance long-term wound healing.

Example 5

Determination of Release Kinetics from Biocide-Containing Film and Permeation Through Hydrogel Matric Example 5.1

Preparation of Hydrogel

A 12.3% (w/v) suspension of polyvinyl alcohol 28-99 (Sigma Aldrich Mowial 28-99, MW about 145,000, 99.0-99.8 hydrolysis) in deionized water is heated under pressure at approximately 115° C. for 30 minutes, cast between glass plates and subjected to one or more freeze-thaw (FT) cycles. Samples of the hydrogel were cut from the gel, blotted with absorbent paper, weighed and desiccated for up to 41 hours.

In order to determine % swelling, samples were placed in a volume of deionized water and allowed to incubate for up to 7 hours, followed by blotting and weight determination.

Figure 10:
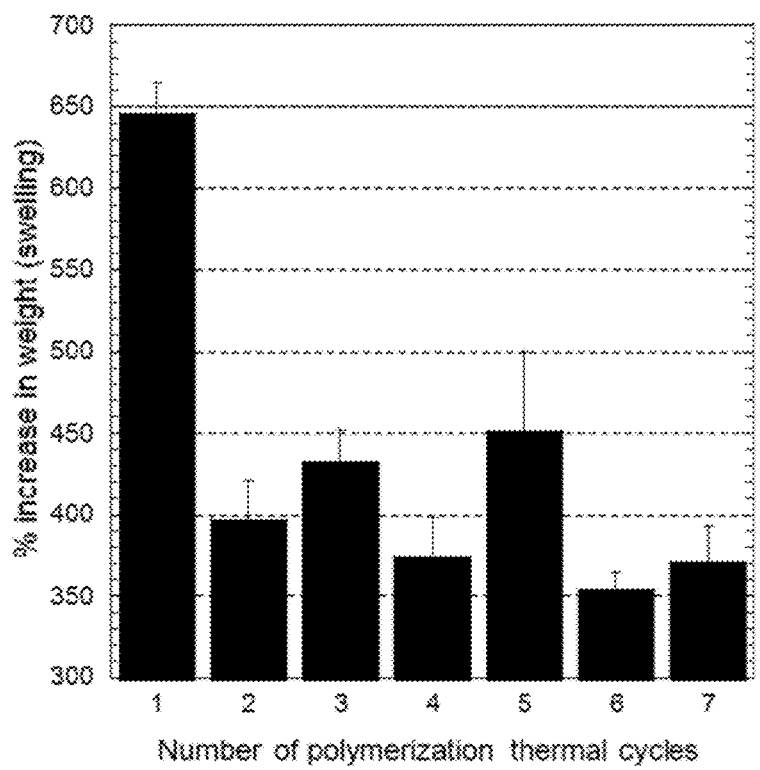
FIG. 10 shows hydrogel swelling for gels undergoing 1-7 freeze-thaw cycles.

Hydrogels subjected to 1-7 FT cycles were evaluated for swelling and visible characteristics. The results are plotted in FIG. 10. The hydrogels lost (mean±standard deviation) 86.5±0.2% of their initial weight in the first 15 hours of desiccation. Within experimental error, no further weight was lost in the next 26 hours. The data in FIG. 10 shows that gels subjected to a single FT cycle achieve the most swelling. These gels are also relatively non-rigid. Hydrogels generally become more rigid with increasing FT cycle, but do not show an appreciable decrease in swelling.

These gels are formed essentially through solids exclusion processes. The hydrogel is held together non-covalently through hydrogen bonding and Van derWaals forces, and some ionic bonding may take place. As such, the gels are considered reversible "physical" gels (as opposed to chemical) and may be disrupted when exposed to sheer forces. A significant advantage of these gels is the lack of chemical modifiers which thus provides a (typically) highly biocompatible hydrogel.

Example 5.2

Permeation of Biocide Through Hydrogels—Diffusion Studies

The Franz diffusion cell is used for studying drug permeation through biological tissue. This cell is made of glass and, during experimentation, is positioned in a heated stir-block so that the temperature of the receptor chamber can be held at skin temperature (34° C.). The receptor chamber is filled with saline (and a non-ionic surfactant may be added) and continually stirred at 600 RPM; temperature and stir rate were calibrated.

For the permeation studies, biocide (F100212E, 5.3% PPA from 10.8.12) was spiked with 14C-Pyruvic acid (14C pyruvic acid sodium salt, 50 μCi, labeled on carbon-1) sodium salt and applied to the hydrogels.

Dissolvable thin film biocide preparations were prepared as Example 1, but the spiked biocide was used at an original film-pour concentration of 20,000 ppm (when the film-pour dries, it loses approximately 25× of its weight through solvent evaporation, and thus the final concentration of the biocide is much higher than the film-pour).

In the permeation experiments, approximately 2×2 cm samples of hydrogels of various freeze-thaw cycles were positioned on the Franz cell between the donor and receptor chamber. The chamber halves were then held tightly together with a pinch-clamp. The receptor chamber was filled with deionized water. Spiked biocide was applied directly to the hydrogel surface or Biocide-containing thin films (6 mm diameter) were cut into 4 pieces and then applied to the superior surface of the hydrogel, in place above the receptor chamber of the diffusion cell. Visual confirmation of dissolution was made upon contact. The chamber was reassembled and the opening of the donor chamber was occluded with Parafilm. Samples of receptor chamber fluid were extracted, with replacement, from the receptor chamber at various times over a period of 0-25 hours of film application. After 25 hours, any remaining solution in the donor chamber was collected. The donor chamber collection and the hydrogel were subjected to liquid scintillation counting in a Packard liquid-scintillation counter with a quench-curve correction being applied to the data.

Figure 11:
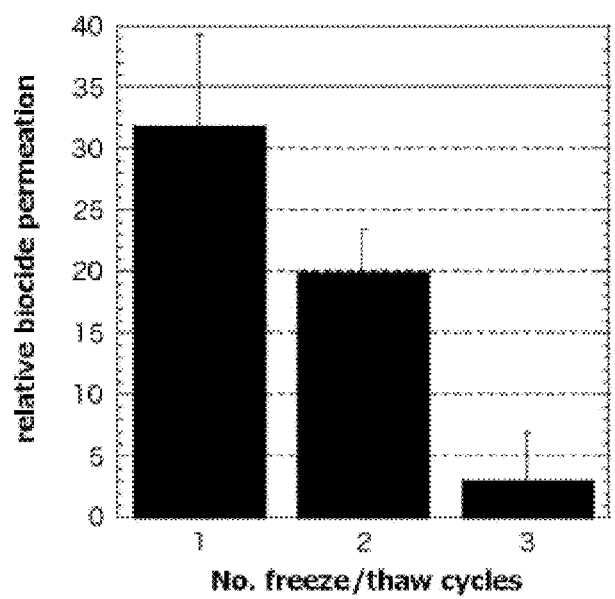
FIG. 11 shows permeation of aqueous biocide through hydrogels of increasing the number of freeze-thaw cycles.

FIG. 11 shows the result of an experiment (a) to assess how increasing the number of FT cycles affects permeation of the spiked biocide through the hydrogels. The biocide was applied in the donor chamber directly to the surfaces of hydrogels that had undergone 1, 2 or 3 FT cycles, and stirred for 19-22 hours, after which the receptor chamber was sampled. The results of FIG. 11 show that multiple freeze-thaw cycles make the hydrogel less permeation to biocide, but that the biocide freely permeates.

Figure 12:
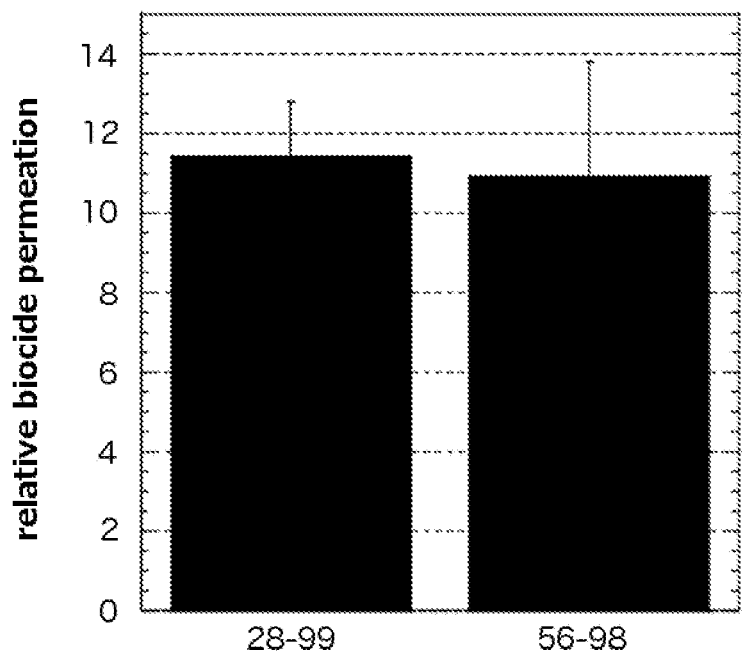
FIG. 12 shows permeation of aqueous biocide through hydrogels of different polymerization and 1 freeze-thaw cycle.

An experiment was performed to assess the effects of substituting different sources of PVA on gel permeation. PVA (Mowiol 28-99, Fluka 10-98 and Fluka 56-98) samplers were used to make the standard 12.3% (w/w) pour which was polymerized with one FT cycle. These PVAs have different degrees of polymerization which provides for variable molecular weight polymers (125K, 61K and 195K). The 10-98 PVA did not gel with one freeze-thaw cycle and so was eliminated from further experimentation. As in experiment (a), aqueous spiked biocide was the applied test material, and permeation was allowed to take place for 24 hours. Assays of the permeation (FIG. 12) showed no statistical difference ($p<0.05$) in the amount of biocide permeating the hydrogels made with 28-99 and 10-98.

Release of spiked biocide from thin films applied to the surface of hydrogels was then assessed in a preliminary experiment. Hydrogels consisting of Mowiol 28-99 and polymerized for one FT cycle were tested. In this study, spiked biocide containing thin films were applied to the surface of the hydrogels, and permeation monitored. The results showed that 96.7±35.4% of the radiolabeled active ingredient in the film permeated the hydrogel by 4 hours. No further permeation was measurable (within experimental error) at 25 hours after film application. Following the study, it was determined that the hydrogel retained 1.7±1.2% of the applied biocide and the donor chamber retained 4.3±3.4% of the applied biocide.

Example 5.3

Permeation of Biocide Through Hydrogels—Inhibition Studies

Kirby-Bauer growth inhibition (or disk diffusion susceptibility testing) is used to quantify the efficiency of antibiotics and/or to test the sensitivity of particular rapidly growing bacteria to an antibiotic.

A bacterial inoculum was prepared from log-phase cultures (ATCC *e. coli* 25922) to a standard density (approximately 1×108 CFU/ml, which is equivalent to a 0.5 McFarland turbidity). The inoculum was applied to a culture dish with Muller-Hinton nutrient agar.

Dissolvable thin film biocide preparations were prepared as Examples 1 or 3, but the spiked biocide was used at an original film-pour concentration of 20,000 ppm (recall that when the film-pour dries, it loses approximately 16-25× of its weight through solvent evaporation, and thus the final concentration of the biocide is much higher than the film-pour, although some is lost through evaporation as evidenced by the acetic acid smell during dry-down).

Samples of hydrogel (single FT cycle) were also used in some experiments where spiked biocide films were applied to the hydrogel surface and the bi-layer sample applied to the culture surface.

Figure 13:
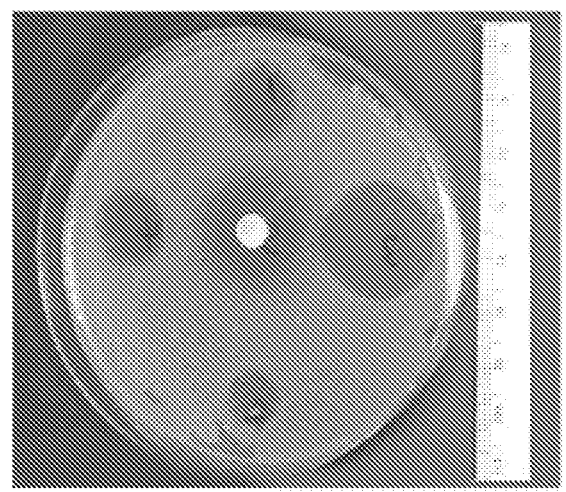
FIG. 13 shows an example of a Kirby-Bauer growth inhibition test plate.

At the time of infection, test materials are applied to the surface of the agar. After a growth a 35-37° C. in air, for period of 16-18 hours, the diameter of the zone of inhibited bacteria growth can be visualized and measured with calipers. A positive control test sample (10 μg gentamicin, BD Sensi-Disc, 6 mm in diameter) is used to confirm the expected behavior of the assay. An example of a plate from the experiments discussed below is shown in FIG. 13.

Experimentation was done to prepare frozen cultures of *e. coli* 25922, and overnight growth conditions to produce an inoculum with the standard 0.5 McFarland density.

Figure 14A:
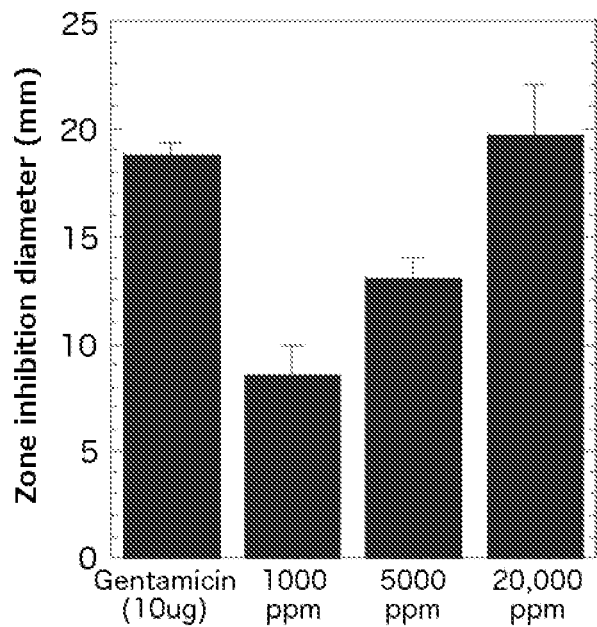
FIG. 14 shows zonal inhibition of dissolving biocidal film (FIG. 14(A)) and dissolving film overlaying hydrogel (FIG. 14(B)).

Kirby-Bauer zonal inhibition assays were performed using the dissolving biocidal films as the test article. At the time of infection, 6 mm diameter samples of dissolving biocidal film (original biocide concentration was 1000, 5000 or 20,000 ppm) were gently placed on the infected agar, as was a 6 mm diameter control Sensi-Disc. The results are shown in FIG. 14(A) (means±s.d.). The control zone inhibition diameter agrees with published quality-control data of 19-26 mm. A dose response is apparent with increasing load of biocide in this study.

Figure 14B:
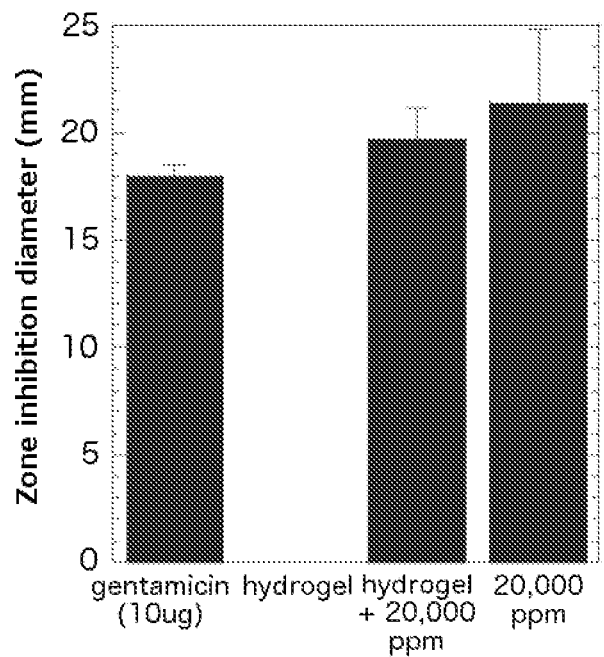

Kirby-Bauer zonal inhibition assays were also performed using dissolvable films placed on top of the hydrogels (1 FT cycle gels) at the time of infection. The results (FIG. 14(B)) are consistent with those in FIG. 14(A) and thus illustrate that the dissolving film active ingredient permeates the hydrogel efficiently. The data also indicate that dissolution of the thin film occurs rapidly.

Example 6

Pullulan Film Containing Peracid

All steps in this formulation were performed at room temperature. Measure out 103.9 ml of water and dispense into a 250 ml beaker with 1" magnetic stir bar. Begin stir at about 10 RPM. Keep beaker covered with aluminum foil to minimize evaporation.

Disperse 0.091 g λ-carageenan slowly into water. Stir for no less than 30 minutes. Confirm that it's fully dispersed before going to the next step.

Measure out 2.18 g of pullulan and slowly dispense into beaker. Stir for no less than 15 minutes. A short time high-speed stirrer may be needed to get the material fully in contact with the water before reducing the speed.

Add 146 μl of polysorbate 80; continue to stir for 15 minutes. This volume of the highly viscous solution is difficult to measure with standard adjustable pipettors, so mass may be measured, and used a density of 1.075 g/ml to determine the volume dispensed. Add 1.17 ml of 1000 ppm pyruvate peracid ("PPA") to mixture and stir for several minutes.

In laminar flow hood, decant the following volumes into the molds in various sizes: 16.8 ml into each of 4 of 6×10 cm molds; 6.7 ml into 6×4 cm molds; 0.28 ml into 1×1 cm molds. All molds are 1.5 mm deep. Leave fan on and light off (patch drawdown is adversely affected by UV light) for at least 12 hours.

When the patches are dry, they release from the mold slightly. Sometimes they have to be coaxed off the silicone mold with tweezers.

Note that when the circular (1.875 inch diameter) patches dry down, they have a weight of about 0.15-0.25 g, and they started at about 5 g. Thus, assuming no peracid loss during drydown, the peracid concentration goes up about 20-30 fold.

The patches may be packed in sterile tin-foil, hand-crimped at the edges. This gives the fragile patch material some mechanical integrity. Store samples patches in 3M Scotchpak MB285 heat sealable polyester film laminate. Cut 9 inch length (6 inch fixed width) of film, fold over lengthwise and impulse seal on 3 edges (using 8" 450 W impulse bag sealer) for about ½ sec at each edge (setting on sealer=7). Insert patch and seal open edge. Then, the patch may be kept refrigerated.

The procedures apply to making films from 100 ppm to 96,000 ppm PPA solution.

Example 7

Peracid Concentration after One Year Storage

Peracid-containing pullulan made from 100 ppm peracid in Example 1 was reconstituted to aqueous solution after one year storage. RQflex reflectometer (sold by EMD-Millipore and developed for measurement of peracetic acid) readings showed that peracid concentration was about 100 ppm with a margin of weighing error and multiple handlings before testing.

Example 8

Peracid Antimicrobial Efficacy after One Year Storage

FIG. 1 shows peracid-containing pullulan made from 100 ppm and 1000 ppm peracid according to Example 1. FIG. 2 shows the result of treating MRSA on blood agar plate with the newly made peracid-containing pullulan film. FIG. 15 shows the result of treating MRSA on blood agar plate with the film after one year storage. As the results show, the film after one year storage still has chemical activity comparable to the newly made film.

Example 9

Removing Pullulan

FIG. 16 shows an example of boronic acid capture resin. A polymeric resin is modified with a phenyl-boronic acid derivative such as 4-aminophenylboronic acid. The resin material is not specific and must simply have a surface functionality that allows for covalent attachment of the boronic acid species. Likewise, the specific boronic acid structure can be varied and only need contain a boronic acid and a functional element for immobilization on the capture resin. The method of immobilization is also not important and could be varied depending on the resin/boronic acid species.

The foregoing embodiments and examples are intended only as examples. No particular embodiment, example, or element of a particular embodiment or example is to be construed as a critical, required, or essential element or feature of any of the claims. Various alterations, modifications, substitutions, and other variations can be made to the disclosed embodiments without departing from the scope of the present invention, which is defined by the appended claims. The specification, including the figures and examples, is to be regarded in an illustrative manner, rather than a restrictive one, and all such modifications and substitutions are intended to be included within the scope of the invention. Accordingly, the scope of the invention should be determined by the appended claims and their legal equivalents, rather than by the examples given above. For example, steps recited in any of the method or process claims may be executed in any feasible order and are not limited to an order presented in any of the embodiments, the examples, or the claims.

What is claimed is:

1. A wound treating matrix comprising at least one layer which is non-aqueous that comprises an antimicrobial composition comprising a carboxylic acid, the peracid of said carboxylic acid, the ester of said carboxylic acid, and an oxidizer in a non-aqueous medium.

2. The wound treating matrix according to claim 1, wherein the non-aqueous layer is biodegradable.

3. The wound treating matrix according to claim 1, wherein the non-aqueous layer is dissolvable.

4. The wound treating matrix according to claim 1, further comprises:
an aqueous layer;
wherein the aqueous layer is separated from the non-aqueous layer prior to use;
wherein in use, the non-aqueous layer is exposed to the aqueous layer, and the antimicrobial composition migrates into the aqueous layer.

5. The wound treating matrix according to claim 4, further comprising a removable fluid-resistant barrier layer for initially separating the non-aqueous layer from the aqueous layer, wherein in use, the barrier is removed to allow contact between the non-aqueous layer and the aqueous layer.

6. The wound treating matrix according to claim 1, wherein the antimicrobial composition is released from the non-aqueous layer when contacted with a water based fluid.

7. The wound treating matrix according to claim 6, wherein the water based fluid is wound exudate.

8. The wound treating matrix according to claim 1, wherein the non-aqueous layer provides a controlled release of the antimicrobial composition when contacted with a water based fluid.

9. The wound treating matrix according to claim 4, wherein the aqueous layer provides a controlled delivery of the antimicrobial composition when contacted with a water based fluid or exudate.

10. The wound treating matrix according to claim 4, wherein the aqueous layer is a hydrogel.

11. The wound treating matrix according to claim 1, further comprising a surfactant.

12. The wound treating matrix according to claim 1, further comprising a stabilizing agent.

13. The wound treating matrix according to claim 1, further comprising an emulsifying agent.

14. The wound treating matrix according to claim 1, wherein the peracid is a peroxy α-ketocarboxylic acid.

15. The wound treating matrix according to claim 14, wherein the peroxy α-ketocarboxylic acid is selected from peroxy α-ketopyruvic acid, peroxy α-ketobutyric acid, peroxy α-ketovaleric acid, or a mixture of thereof.

16. The wound treating matrix according to claim 1, further comprising a liquid-impermeable backing layer adjacent to the non-aqueous layer.

17. The wound treating matrix according to claim 16, wherein the backing layer is adhesive-coated and provides an adhesive-coated margin around the non-aqueous layer.

18. The wound treating matrix according to claim 1, wherein the non-aqueous layer further comprises a polymer and the peracid is chemically bonded to the polymer.

19. A method for treating a wound, comprising providing the wound treating matrix according to claim 1, and topically applying the wound treating matrix to the wound.

20. A wound treating matrix according to claim 1 further comprising at least one layer comprising a wound treating agent.

21. The wound treating matrix according to claim 20, wherein the wound treating agent is one or more of (1) hemostatic agent, (2) anti-inflammatory drug, (3) analgesic drug, (4) angiogenesis promoters.

22. A wound treating matrix comprising a wound treating agent and a peracid composition according to claim 1, wherein the peracid composition is encapsulated in a biocompatible structure.

23. The wound treating matrix of according to claim 22, wherein the biocompatible structure is a nanostructure, liposome, or micelle.

24. A wound treating matrix according to claim 1 further comprising a polymer and wherein the peracid is chemically bonded to the polymer.

25. The wound treating matrix according to claim 24, wherein the polymer is polyvinyl.

26. The wound treating matrix according to claim 24, wherein the polymer is polyurethane.

27. The wound treating matrix according to claim 24, wherein the polymer is a resin or protein.

* * * * *